United States Patent [19]

Sanyal

[11] Patent Number: 5,421,346
[45] Date of Patent: Jun. 6, 1995

[54] RECOVERY OF HUMAN UTERINE CELLS AND SECRETIONS

[75] Inventor: Mrinal K. Sanyal, Houston, Tex.

[73] Assignee: Baylor College of Medicine, Houston, Tex.

[21] Appl. No.: 155,797

[22] Filed: Nov. 23, 1993

[51] Int. Cl.⁶ ............................................. A61M 25/00
[52] U.S. Cl. .................................................... 128/750
[58] Field of Search ............... 128/760, 761, 763, 765, 128/768, 769, 749, 750, 756; 604/27, 35, 55, 270, 271; 606/119, 123, 193

[56] References Cited

U.S. PATENT DOCUMENTS

| | | | |
|---|---|---|---|
| 3,948,270 | 4/1976 | Hasson | 604/55 |
| 4,243,040 | 1/1981 | Beecher | 604/271 X |
| 4,245,653 | 1/1981 | Weaver | 128/750 |
| 4,693,704 | 9/1987 | Ogita | 604/55 |
| 4,775,362 | 10/1988 | Kronner | 604/55 X |
| 4,966,162 | 10/1990 | Wang | 128/756 X |
| 5,300,023 | 4/1994 | Lowery et al. | 604/55 X |

Primary Examiner—Sam Rimell
Attorney, Agent, or Firm—Bush, Moseley, Riddle & Jackson

[57] ABSTRACT

Apparatus and procedural methods for dislodging cells and/or secretions from the uterine walls and cavity and removing them for various diagnostic purposes includes a barrel having a holder/stabilizer adjustably mounted on its upper end and a stopper assembly including an inflatable element mounted on its outer end. The barrel is positioned such that the stopper assembly is seated in the cervix, and the element is inflated to seal the same and to lock the stopper therein. Then a catheter having spray openings, or a stem having a brush on its outer end, is inserted through the barrel and operated to dislodge cells, which then are removed by aspiration or the like.

12 Claims, 2 Drawing Sheets

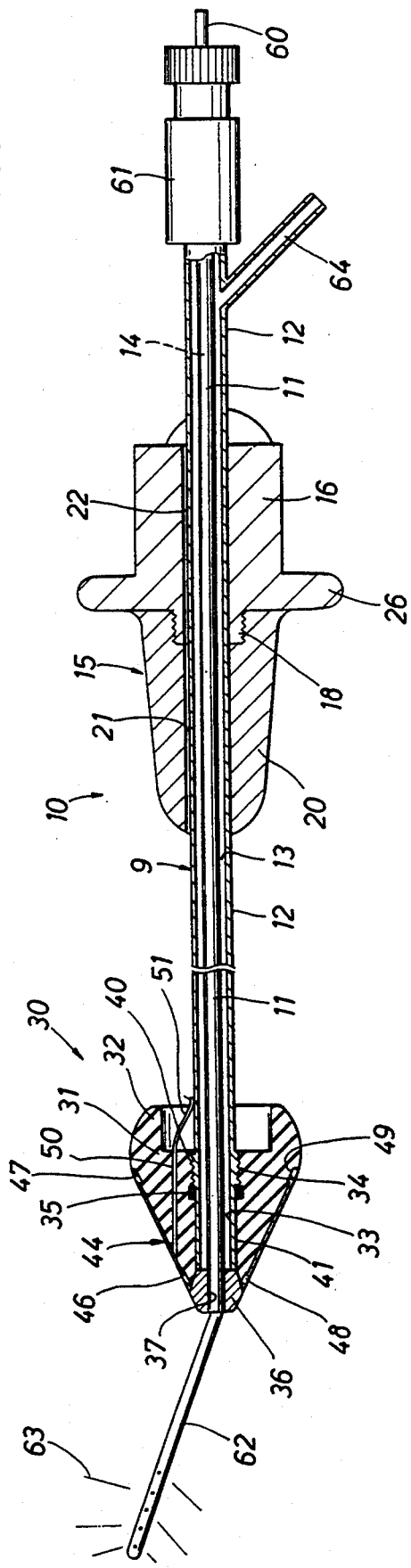

RECOVERY OF HUMAN UTERINE CELLS AND SECRETIONS

FIELD OF THE INVENTION

This invention relates generally to a device for recovering cells and secretions from the walls of the uterine cavity of a human, and particularly to a device and method for this purpose which is designed such that cell recovery is relatively safe, non-traumatic, and does not cause injury to the patient.

BACKGROUND OF THE INVENTION

The human uterus is an important reproductive organ, and its optimal functioning is central to human development. There is a compelling need in this art for a better understanding of the biological processes that regulate uterine physiology, and those processes which are associated with early embryonic development. To conduct studies, apparatus is needed to extract endometrial cells and secretions from the uterine cavity in a non-traumatic and safe manner, and in a way that can be routinely applied to ambulatory subjects. Such cells and secretions can then be analyzed for diagnosis of various uterine diseases, such as precancerous and cancerous conditions, endometrial disorders, and causes for spontaneous abortions. The uterine material may also be used to identify factors that promote embryogenesis. In addition, uterine endometrial cells can be co-cultured with preembryo cells of the in vitro fertilization (IVF) procedure for improvement in pregnancy outcome. Such advances in IVF procedure will permit prevention of hereditary diseases has greater success.

An object of the present invention is to provide a new and improved apparatus and methods for the non-traumatic recovery of cells and secretions from the human uterine cavity.

Another objective of the present invention is to provide new and improved devices and methods for uterine cell aspiration which do not cause injury and can be applied routinely to ambulatory subjects.

Still another object of the present invention is to provide new and improved apparatus of the type described which removes cells and materials from the human uterus to permit disease diagnosis, improvement in IVF procedures for pregnancy initiation, and/or preembryo biopsy.

SUMMARY OF THE INVENTION

These as well as other objects are attained in accordance with the present invention through the provision of an apparatus which includes a concentrically arranged assembly of relatively rigid tubes which define a barrel having a central passage through the inner tube and an annular passage in the space between the tubes. A holder and stabilizer means are adjustably mounted on an outer end portion of the barrel, and a stopper means which carries an inflatable element is mounted on the inner end of the barrel. With the stopper means positioned in the cervix, the inflatable element is pressurized so that it attains a greater diameter on the inner side of the cervical opening and thus holds the stopper means in place to prevent leakage of fluids back into the vagina.

A means such as a catheter having spray openings in its outer end portion then is inserted through the inner tube and into the uterus. Flow of a saline solution is used to dislodge cells and secretions from the uterus walls. The stopper means has ports which allow the solution to flow into the annular passage in the barrel where they pass via a return line to a sterile container. In the alternative, a soft bristle brush on a stem can be inserted through the inner tube so that the uterus walls can be brushed gently to dislodge cells and the like. The materials then are recovered by a saline wash as noted above. The fluids containing dislodged endometrial cells and dissolved secretions also can be aspirated out of the uterine cavity by suction through the annular space between the tubes, or by use of a separate, open-ended catheter that is inserted through the center tube. Thus the present invention provides a uterine cell removal device and method which are non-traumatic and which does not cause injury to human subjects. The invention permits disease diagnosis, improvement in IVF pregnancy initiation, and preembryo biopsy for prevention of hereditary diseases.

BRIEF DESCRIPTION OF THE DRAWINGS

The present invention has the above as well as other objects, features and advantages which will become more clearly apparent in connection with the following detailed description of a preferred embodiment, taken in conjunction with the appended drawings in which:

FIG. 1 is a side elevational view of the present invention with some parts in cross-section;

FIG. 6 is a top view of the assembly of this invention.

DETAILED DESCRIPTION OF A PREFERRED EMBODIMENT

Figures 2A, 2B:
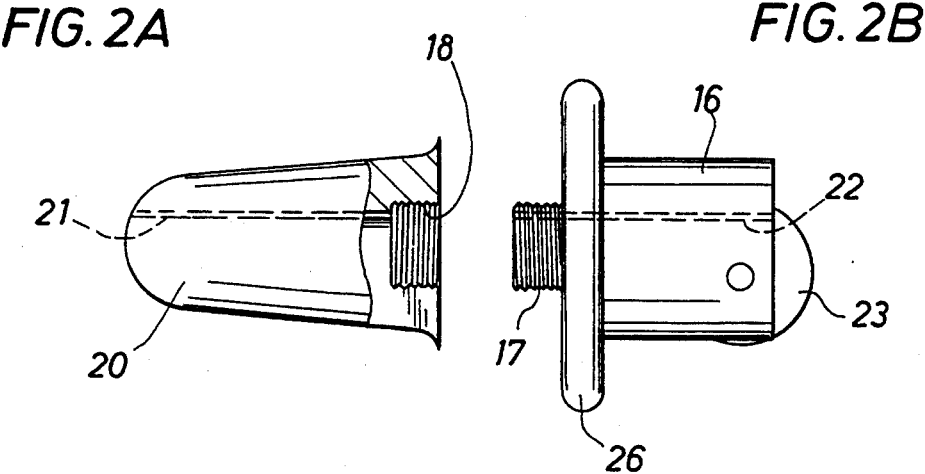
FIGS. 2A and 2B are exploded views of the holder and stabilizer components.
Figure 3:
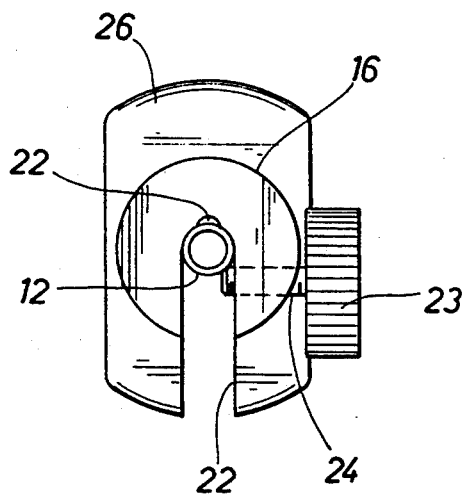
FIG. 3 is a rear view of the holder shown in FIG. 2B.

Referring initially to FIG. 1, the uterine cell or secretion removal apparatus of the present invention is indicated generally at 10, and includes a pair of concentric tubes 11, 12 that preferably are made of stainless steel or a relatively rigid plastic material which forms a barrel 9. The annular space 13 between the tubes 11, 12 provides an internal flow path which is in addition to the flow path provided by the bore 24 of the inner tube 11. A combination holder and stabilizer assembly 15 is slidably and adjustably mounted on the outer end portion of the barrel 9 and includes a holder member 16 by which the assembly can be manipulated, and a stabilizer 20 which fits in the vaginal opening to centralize the barrel 9 during use. The holder member 16 has a threaded boss 17 by which it can be attached to a threaded socket 18 in the stabilizer 20. Such threaded coupling enables the stabilizer 20 to be removed from the holder member 16 and replaced with other stabilizers having alternative shapes and sizes. The stabilizer 20 and the holder member 16 both have downwardly opening slots 21, 22 (FIG. 3) which extend throughout their length to allow them to be simultaneously and completely removed from the barrel 9 and then replaced as a unit. A lock screw 23 threads into a hole 24 in the side of the holder member 16 and bears against the outer tube 12 in order to hold the assembly in position on the barrel 9 at various selected positions therealong. An outward directed flange 26 on the holder member 16 limits movement of the apparatus 10 toward the cervix.

A stopper assembly indicated generally at 30 in FIG. 1 seals the cervix during cell or secretion removal and is mounted on the outer or distal end of the barrel 9. The stopper body 31, which preferably is made of a relatively soft and pliable plastic material, is generally wedge shaped and has a flange 32 which limits forward movement into the cervix. The body 31 has an inner bore 33 which is threaded at 34, and is provided with an internal groove which carries a seal ring 35. The outer end of the bore 33 is closed by a nose 36 which has a central opening 37 and a plurality, for example three, additional openings 38 (FIG. 4) located radially outward thereof. As shown in FIG. 1, the outer portion of the tube 12 has a male thread 40 which screws into the body threads 34, and an outer end portion 41 which engages the rear face of the nose 36. The inner tube 11 extends into the opening 37 of the nose 36 and terminates substantially flush with its forward end. The openings 38 communicate with the annular space 13 between the inner and outer tubes 11, 12, and the seal ring 35 prevents fluid leakage.

Figures 4, 5:
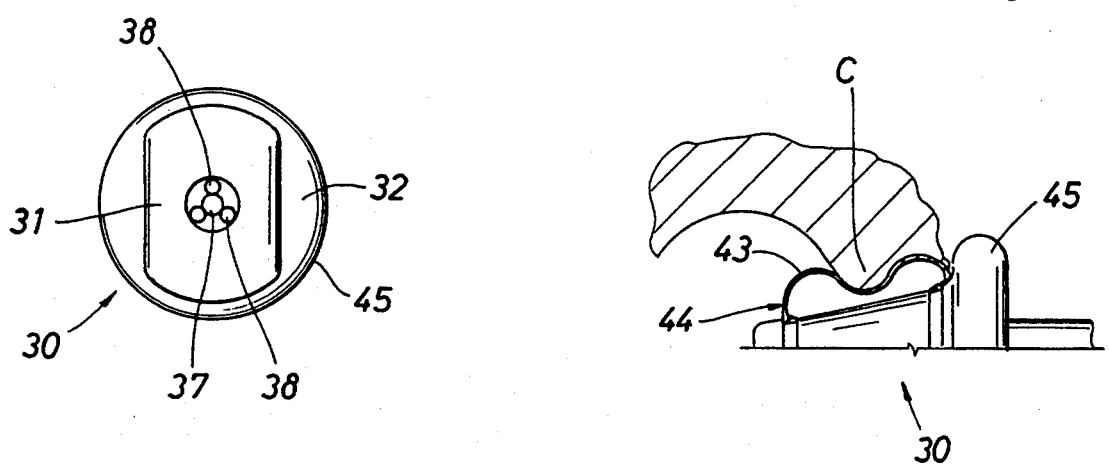
FIG. 4 is a front view of the stopper assembly of the present invention.
FIG. 5 is a fragmentary side view of the stopper assembly with its balloon inflated.

To provide additional sealing of the cervix and to hold the stopper body 31 therein during cell removal procedures, an elastomer balloon member 44 is mounted on the body. The balloon member 44 has the relaxed shape of a frusto-conical sleeve, and has inner and outer flanges or thickened regions 46, 47 that engage tightly in grooves 48, 49 which extend entirely around the body 31. An inflation passage 50 is connected to a small line 51 which extends along the top of the outer tube 12 as shown in FIG. 6, and then through grooves 52, 53 in the stabilizer 20 and the holder 16, respectively. Inflation pressure for the balloon 44 is applied via a coupling 55 to the line 51 and thus to the interior of the balloon to cause it to bulge outward as shown in FIG. 5 for purposes to be described in further detail below.

A connector 61 seals the outer ends of both the inner and the outer tubes 11, 12 as well as the annular space 13 therebetween so that flow through such annulus must be through the return line 64. As shown in FIGS. 1 and 6, a catheter 60 can be inserted through the bore 19 of the inner tube 11 and into the uterine cavity. Preferably the outer end portion of the catheter 60 is shaped so as to be off-axis, such shape being then retained by its shape memory so that rotation thereof can be used to amplify the flushing procedure. The outer portion 62 of the catheter 60 has a plurality of small spray openings 63 which are used to dislodge cells from the uterine walls.

USE AND OPERATION

In use of the present invention to recover uterine cells and secretions, the stopper assembly 30 and the front portion of the barrel 9 are inserted into the vagina until the stopper body 31 is located in the cervix. The distance between the holder flange 26 and the stopper flange 32 will have been adjusted and fixed by the set screw 23 so that the stabilizer 20 is comfortably within the opening of the vagina to maintain the barrel 9 generally centered. The cervix then is sealed off by inflation of the balloon 44 with pressure applied through the line 51 and the connector 55. As shown in FIG. 5, the balloon 44 expands outward along radial paths of least resistance such that the innermost portion 43 is inflated to a larger diameter which, in effect, locks the stopper assembly 30 in the position shown, since this portion is inside or beyond the surrounding tissue at C. With the balloon 44 inflated, leakage from the uterine cavity past the stopper assembly 30 is prevented.

A catheter 60 then is inserted through the seal connector 61 and the bore 14 of the inner tube 11 of the barrel 9 until its end portion 62 protrudes from the nose 36 of the stopper assembly 30 into the uterine cavity. A saline solution or a culture medium then is pumped through the catheter 60 and out of the spray openings 63 to cause cells and secretions to be dislodged from the uterine walls. The solution or medium is aspirated via the opens 38 (FIG. 4), the annulus space 13 and the return line 64 to where they are stored in a sterile container (not shown). The washing or flushing action of the spray jets 63 normally will dislodge a sufficient number of cells from the uterine walls for the purposes of this invention. In an alternative procedure a soft bristle brush (not shown) can be inserted through the tube 11 on a stem and used to dislodge cells by a gentle brushing action. Then the brush is withdrawn and the cells recovered by washing. The fluid which contains the dislodged cells (endometrial) and dissolved secretions also can be aspirated out by vacuum or suction, either through one of the tubes 11 of 12, or through use of a separate catheter run through the inner tube 11. Once these materials are obtained, the balloon 44 is deflated by releasing the pressure on the line 51, and the apparatus removed.

It now will be recognized that a new and improved uterine cell and/or secretion removal device and method have been disclosed. The device is safe and non-traumatic, and can be routinely applied in ambulatory patents. The invention enables uterine secretions and cells to be analyzed for diagnostic application of various uterine diseases, such as precancerous and cancerous conditions, endometrial disorder, and spontaneous abortions. The uterine materials also can be used to identify factors that promote embryogenesis. Furthermore, uterine (endometrial) cells can be co-cultured with preembryos of the IVF fertilization procedure for improvement in pregnancy outcome. These advances in IVF procedures will permit biopsy of the preembryo and diagnosis of genetic disorders more accurately in order to prevent hereditary diseases with greater success. Since certain changes or modifications may be made in the disclosed embodiments without departing from the inventive concepts involved, it is the aim of the appended claims to cover all such changes and modifications falling within the true spirit and scope of the present invention.

What is claimed is:

1. Apparatus for use in recovering cells and other matter from the human uterus, comprising: barrel means including concentric outer and inner tubular members having an annular passageway therebetween, said barrel means having an outer portion and an inner end; holder means fixed on said outer portion; stopper means mounted on said inner end and adapted to seat in the cervix and prevent further inward movement; inflatable means on said stopper means to seal off the cervix; means adapted to be inserted through said inner tubular member and positioned so that a portion thereof extends into the uterus for dislodging cells from the walls thereof; and means for removing dislodged cells via said annular passageway.

2. The apparatus of claim 1 wherein said stopper means has a conically tapered section, said inflatable means being mounted on said section and adapted when inflated to temporarily lock said stopper means in said cervix.

3. The apparatus of claim 2 further including an inflation line extending along said barrel member from a location outside said holder means to a port inside said inflatable means, said line being operable to allow inflation and deflation of said inflatable means.

4. The apparatus of claim 3 wherein said inflatable means includes an elastomer sleeve having thickened regions on its opposite ends which engage in recess means in said stopper means.

5. The apparatus of claim 2 wherein said stopper means includes flange means for limiting entry into said cervix.

6. The apparatus of claim 1 further including stabilizer means attached to said holder means, said holder and stabilizer means having slot means to allow complete removal thereof from said barrel means.

7. The apparatus of claim 6 further including releasable lock means on said holder means for fixing said holder means and said stabilizer means at a selected position along said barrel which provides a desired longitudinal spacing with respect to said stopper means.

8. The apparatus of claim 1 wherein said cell dislodging means includes a catheter having a closed outer end and a plurality of flow ports spaced from said outer end to create jets of solution which dislodge cells.

9. The apparatus of claim 1 wherein said cell dislodging means includes a brush on the outer end of a stem, said brush being operable to dislodge cells from a uterine wall.

10. A method of recovering cells and other matter from the human uterus, comprising: providing a barrel having inner and outer tubular members which provide concentric inner and outer pathways; said barrel having a stopper means on the distal end thereof carrying an inflatable member on said stopper; positioning said barrel in the vagina and the stopper means and inflatable member in the cervix; inflating said inflatable member to seal the cervical opening and temporarily lock said stopper means therein; inserting an instrumentality through said inner tubular member and into the uterus; using said instrumentality to remove cells and other matter from the walls of the uterus; and recovering said cells and matter from the uterus through said outer pathway.

11. The method of claim 10 wherein said instrumentality is a catheter having an outer end section and flow ports in said outer end section whereby sprays of saline solution out of said ports as a result of flow of solution through said catheter can be used to remove said cells and matter.

12. The method of claim 10 wherein said instrumentality is a soft bristle brush inserted through said barrel and used to brush cells and matter from the uterine walls.

* * * * *